United States Patent [19]

Nelson

[11] 4,259,067
[45] Mar. 31, 1981

[54] COMBINED SALIVA EJECTOR, TONGUE RETRACTOR AND THROAT PROTECTOR

[76] Inventor: David P. Nelson, 6303 Osgood Ave. North, Stillwater, Minn. 55082

[21] Appl. No.: 18,032

[22] Filed: Mar. 6, 1979

Related U.S. Application Data

[63] Continuation-in-part of Ser. No. 844,635, Oct. 25, 1977, abandoned.

[51] Int. Cl.³ .............................................. A61C 17/04
[52] U.S. Cl. ....................................... 433/93; 433/138
[58] Field of Search ................... 433/93, 96, 91, 136, 433/138, 140; 128/12, 15

[56] References Cited

U.S. PATENT DOCUMENTS

| 443,512 | 12/1890 | Gash | 433/93 |
|---|---|---|---|
| 1,042,133 | 10/1912 | Marshall | 433/93 |
| 2,644,234 | 7/1953 | Scott | 433/94 |
| 2,885,783 | 5/1959 | Golden | 128/12 |
| 2,937,445 | 5/1960 | Erickson | 433/93 |
| 3,090,122 | 5/1963 | Erickson | 433/93 |
| 3,324,855 | 6/1967 | Heimlich | 433/91 |
| 3,396,468 | 8/1968 | Dayhoff | 433/93 |
| 3,758,950 | 9/1973 | Krouzian | 433/91 |
| 4,053,984 | 10/1977 | Moss | 433/93 |

FOREIGN PATENT DOCUMENTS

| 1108049 | 1/1956 | France | 433/93 |

Primary Examiner—Gene Mancene
Assistant Examiner—John J. Wilson
Attorney, Agent, or Firm—Merchant, Gould, Smith, Edell, Welter & Schmidt

[57] ABSTRACT

A dental device for isolating a region of the mouth in which dental operations are to be performed includes a frame to retain the device in the mouth in substantially vertical orientation between the inside of the lower teeth and the patient's tongue. The frame includes a palatal member that engages the roof of the mouth and a lingual member connected to the palatal member to engage the mouth generally at the mouth floor. The palatal and lingual members are resiliently biased in a direction away from each other so that upon placement of the device in the mouth the device is in compressive engagement between the mouth floor and roof. The lingual member has a first portion disposed generally above the mandibular occlusal plane and extending outward to engage the lower teeth and a second portion extending generally downward below the mandibular occlusal plane. A shield member is affixed to the second portion and is sized to shield the tongue from the lower teeth. The tongue pressing against the shield member serves to stabilize the device in the mouth against lateral displacement with the second portion of the lingual member retained against the inside of the gums below the teeth.

9 Claims, 13 Drawing Figures

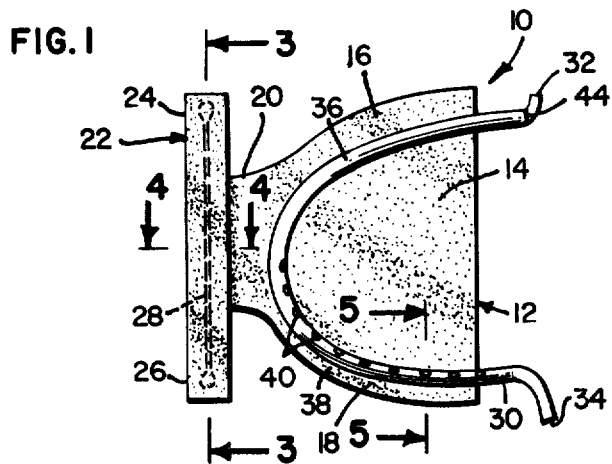
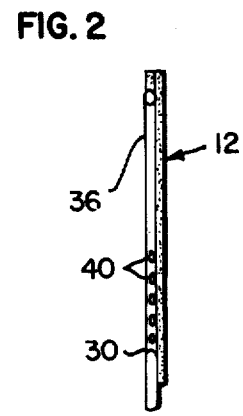
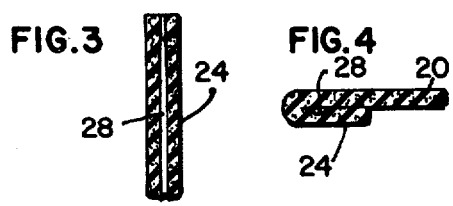
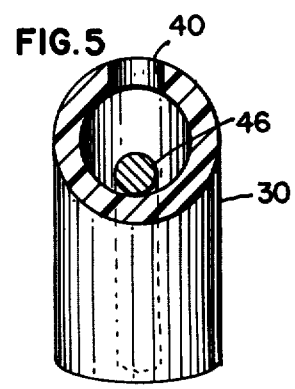
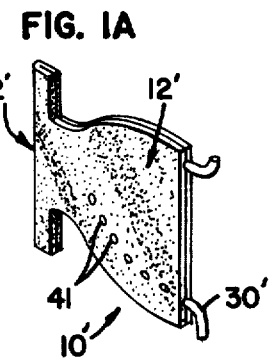
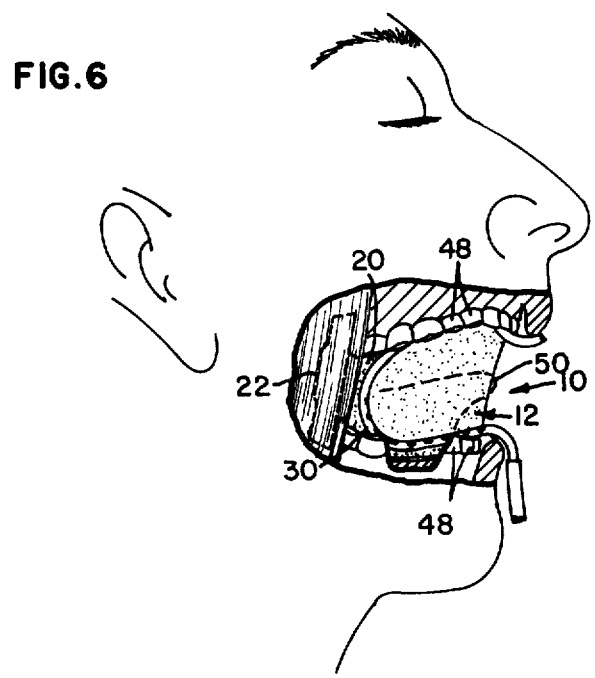
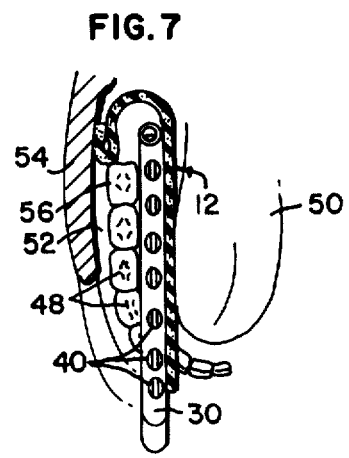

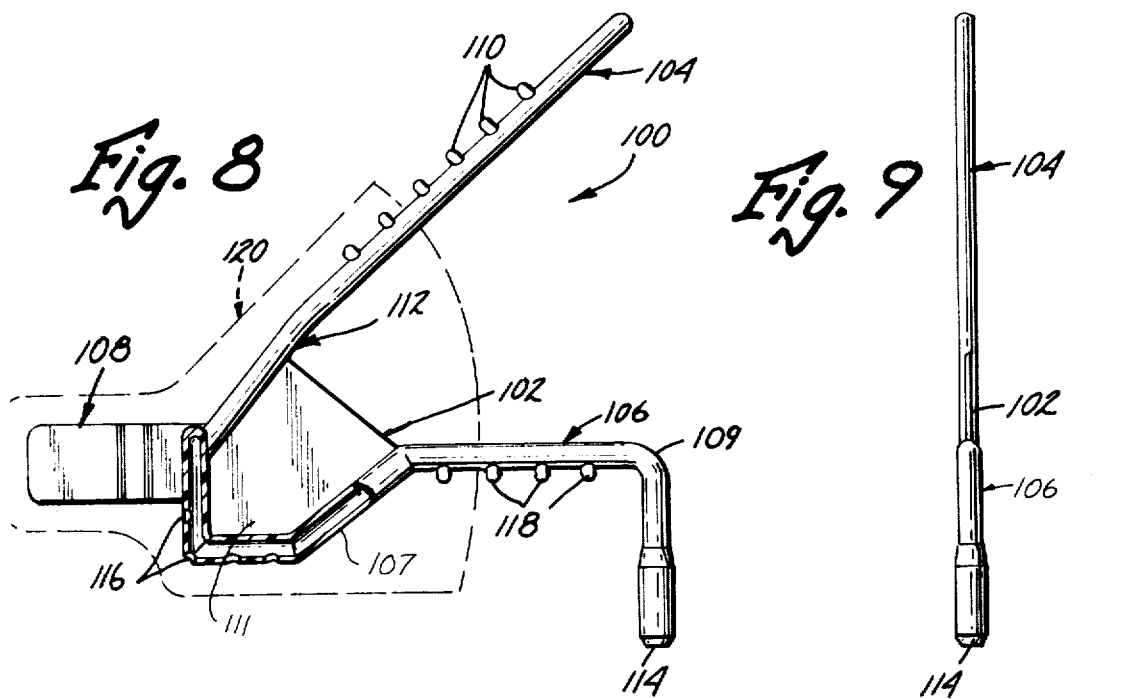
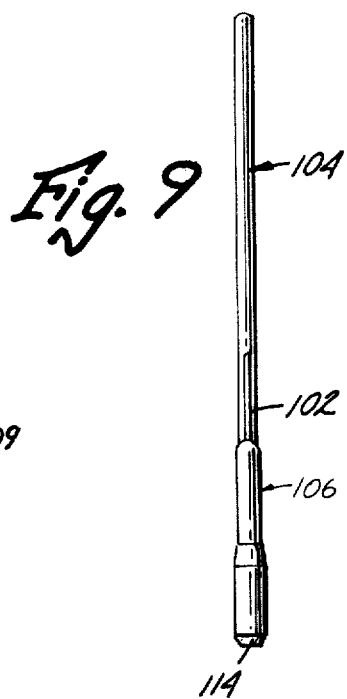
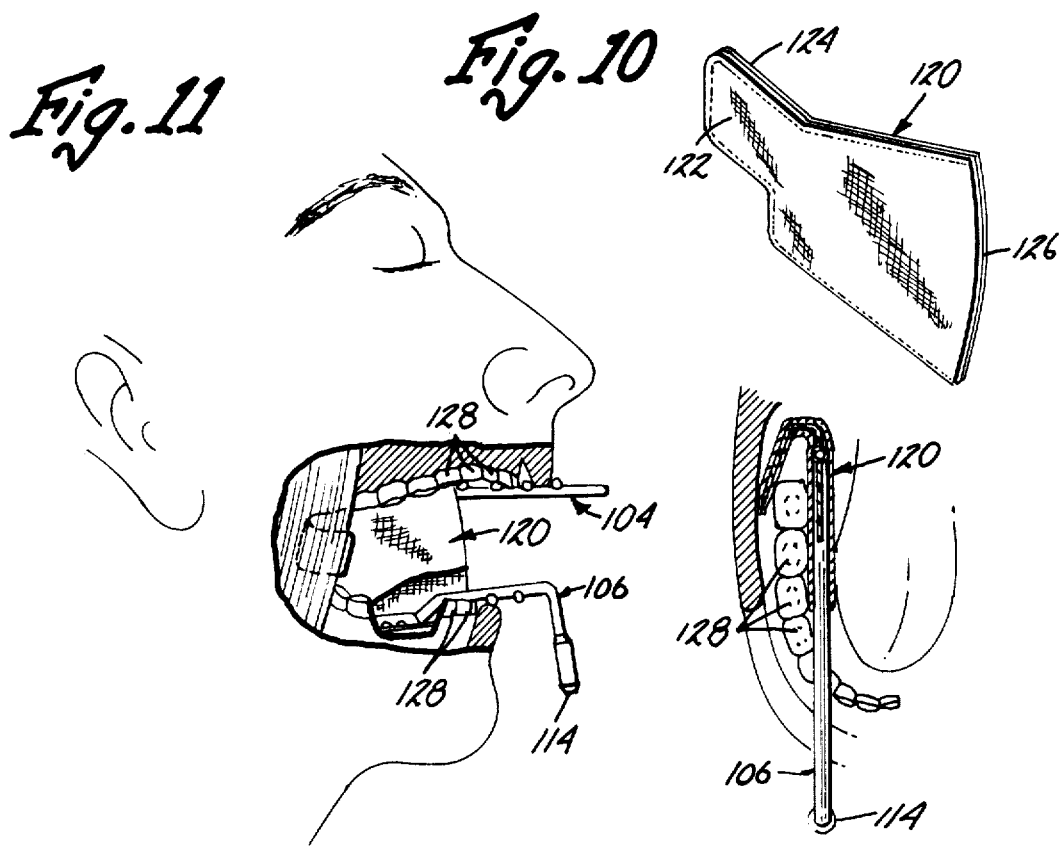

COMBINED SALIVA EJECTOR, TONGUE RETRACTOR AND THROAT PROTECTOR

This application is a continuation-in-part of Ser. No. 844,635 filed Oct. 25, 1977, now abandoned.

BACKGROUND OF THE INVENTION

The present invention relates broadly to a dental device for isolating a region of the mouth in which dental operations are performed, and, in particular, to a dental device which functions as a tongue retractor, throat protector, and saliva ejector and mouth prop.

In the conduct of dental operations, it is desirable to prevent the patient's tongue from interfering with the dental procedures. Additionally, a patient may experience a considerable amount of pain and discomfort if his tongue happens to come into contact with high speed dental drilling apparatus. This problem is particularly significant when the dental patient is a small child who has more difficulty keeping his or her tongue out of the way. The problem is also significant in situations where the patient is an adult since it is extremely tiring for the patient to hold his tongue in a particular place for extended periods of time and in situations where the dental work must be done in very close proximity to the tongue.

In addition, a patient's head is typically tilted backward for the dental work. The patient is thus extremely susceptible to debris generated during the dental operations falling into his throat. This situation is also extremely uncomfortable for the patient and creates the hazard of debris lodging in the breathing passageway. Thus, it is desirable to have a dental device that shields and retracts the tongue from the work area and in addition protects the throat opening.

A number of prior art devices have been developed to accomplish one or more of these desirable functions. These prior art devices, however, have a number of disadvantages and, consequently, have not been widely accepted in the field of dentistry. For example, one such prior art device is referred to as a rubber dam. The rubber dam is a sheet of rubber material that is secured to a frame and placed entirely over the patient's mouth. A hole is cut in the rubber dam at the location of the work area to expose that portion of the mouth in which the dental operations are to be performed. Since the patient's entire mouth is closed by the rubber dam, the patient often experiences an uncomfortable gagging sensation or feels that his breathing is inhibited. Additionally, the rubber dam is phychologically depressing to the patient by virtue of its size and the hardware that must be utilized to secure the rubber dam in place. Thus, the rubber dam has found limited application to those situations in which the patient is placed under total anesthesia. The rubber dam has an added disadvantage in that the rubber sheet and hardware represent a continuing sterilization problem.

Another prior art device is disclosed in the patent to Erickson U.S. Pat. No. 3,090,122. The Erickson device is molded of a waterproof or liquid impervious flexible material such as rubber or plastic. The device has a central depressed portion in which saliva pools and is collected. The marginal edges of the Erickson device are adapted to provide a sealing engagement with the roof and floor of the mouth with the device between the patient's teeth and tongue. The patient may experience a gagging sensation with the Erickson device due to the sealing engagement of the device with the roof of the mouth. The saliva and debris are collected through a pair of apertures positioned basically in the center of the Erickson device. With the patient's head typically tilted backward, saliva and debris tends to pool or collect along the floor of the mouth or lower edge portion of the dental device. With the saliva and debris collecting apertures disposed somewhat centrally on the device, saliva removal may not necessarily be very efficient. The Erickson device is a relatively high cost item of dental equipment, and as with the rubber dam apparatus, must be effectively sterilized prior to each use thereof. The Erickson device also includes a bite block adapted to engage by the patient's teeth to aid in holding the mouth open. Finally, when the dentist uses an auxiliary vacuum ejector, rubber or plastic material tends to be drawn against the ejector blocking the opening. This is extremely annoying to both the dentist and the patient.

The present invention eliminates the disadvantages of the prior art devices in that it is a dental device that combines the features of tongue retraction, throat protection, and saliva ejection in a device that is comfortably worn and easily tolerated by the patient. In keeping with the modern trend in medical and dental devices, the present invention is a low-cost disposable device. The present invention is formed of a foam elastomeric material having liquid absorbent properties. The present invention is provided with a wire frame that maintains the device in place in the mouth in addition to aiding in holding the mouth open. The present invention maximizes the efficiency of saliva and debris rejection by providing a plurality of apertures along the lower or lingual edge thereof where the saliva tends to pool or collect. Additionally, the foam elastomeric material absorbs saliva which is then ejected. The device of the present invention is firmly held within the mouth, however, the foam elastomeric material is nevertheless comfortable to the patient. The dentist can simply discard the device of the present invention after a single use, eliminating time consuming sterilization procedures and insuring a sanitary device at each use thereof.

SUMMARY OF THE INVENTION

The present invention is a dental shield for isolating a region of the mouth and adapted to be placed in the mouth in substantially vertical orientation. The shield includes a shield member adapted to be disposed between the patient's teeth and tongue. Connected to the shield member generally at the bottom thereof is a lingual member having a plurality of projections spaced apart thereon to engage selected ones of the patient's lower teeth. The palatal member is connected to the shield member generally at the top thereof and the palatal member also has a plurality of projections to engage selected ones of the patient's upper teeth. The lingual and palatal members are connected to the shield member to permit movement generally toward and away from each other. Means are provided for resiliently biasing the palatal and lingual members in a direction away from each other whereby upon placement of said shield within the mouth said shield is placed in compressive engagement between the roof and floor of the mouth. In the preferred embodiment the lingual member has a tubular portion with an opening in one end thereof and a plurality of apertures disposed therein whereby saliva may be collected through the apertures and ejected from the mouth through the opening.

The present invention is a dental device that includes a shield member formed of a flexible elastomeric material which is sized to be placed in a mouth in substantially vertical orientation between the inside of the teeth and the tongue. The shield member includes a first member having a palatal edge portion, a lingual edge portion and a central portion. The palatal edge portion and lingual edge portion are adapted to engage the roof and floor of the mouth, respectively. The central portion of the first member shields and retracts the tongue. Throat protecting member extends rearwardly from the first member and is adapted to be folded forwardly in a direction toward the first member and to extend between the distal surfaces of the rear molars and the interior border of the ascending ramus of the mandible at one side of the mouth. Means for collecting saliva and removal thereof is affixed to the shield member along the lingual edge portion. A frame means is affixed to the shield member to secure the shield member within the mouth and provide structural support for the flexible elastomeric material.

In one embodiment, the shield member is formed of a foam elastomeric material having liquid absorbent properties. In its broadest sense, however, the shield member may be of any suitable material adapted to retract the tongue. The saliva collecting and removal means is a tube having apertures therein affixed along the lingual edge portions of the shield member. When viewed in side elevation, the tube is substantially C-shaped and has a first portion attached to the palatal portion of the shield member, a second portion affixed to the lingual edge portion, and a third central portion. The tube may be imbedded within the foam material and apertures may be provided in the foam material substantially aligned with the apertures in the saliva collecting and removal tube.

The frame means is a wire having a first portion disposed along the palatal edge portion of the shield and a second portion disposed along the lingual edge portion. The first and second wire portions compressively engage the roof and floor of the mouth, respectively. In the preferred embodiment, the wire is disposed within the saliva and debris ejection tube. Apertures are provided in the tube essentially from the mid-point of the shield member downwardly along the lingual edge portion.

The dental device of the present invention can be comfortably held within the mouth with the palatal and lingual edge portions of the shield member engaging the roof and floor of the mouth, respectively, and with the shield member in conjunction with the wire frame protecting and retracting the wire tongue. The throat protecting member prevents debris from falling into the patient's throat while the patient's head is tilted rearward. The saliva ejection tube has apertures disposed in the region wherein saliva will collect. The wire frame also assists in holding the patient's mouth open. Saliva collection and removal is facilitated by the provision of the flexible elastomeric material having liquid absorbent properties. These and other advantages of my invention will become apparent with reference to the accompanying drawing, detailed description of the preferred embodiment and claims.

BRIEF DESCRIPTION OF THE DRAWINGS

FIG. 1 is a view in side elevation of the dental device of the present invention;

FIG. 1A is a view in perspective of an alternative embodiment of the present invention;

FIG. 2 is a front elevation view of the dental device of the present invention illustrated in FIG. 1;

FIG. 3 is an enlarged partial sectional view taken generally along the line 3—3 of FIG. 1;

FIG. 4 is an enlarged sectional view taken generally along the line 4—4 of FIG. 1;

FIG. 5 is an enlarged sectional view taken generally along the line 55 of FIG. 1;

FIG. 6 is a view in side elevation showing the positioning of the dental device in the present invention in a patient's mouth, with a portion of the anatomy broken away to more specifically illustrate the device placement;

FIG. 7 is a fragmentary enlarged plan view of the dental device of the present invention shown in place in the patient's mouth;

FIG. 8 is a view in side elevation of an alternative embodiment of the dental device of the present invention;

FIG. 9 is a front elevational view of the alternative embodiment of the dental device of the present invention illustrated in FIG. 8;

FIG. 10 is a view in perspective of a cover member that may be utilized in connection with the alternative embodiment of the present invention shown in FIGS. 8 and 9;

FIG. 11 is a view in side elevation showing the positioning of the dental device of the embodiment of FIG. 8 disposed in a patient's mouth with a portion of the anatomy broken away to more specifically illustrate the device placement;

FIG. 12 is a fragmentary enlarged plan view of the dental device of the embodiment of FIG. 8 shown in place in the patient's mouth.

DETAILED DESCRIPTION OF THE PREFERRED EMBODIMENT

Referring to the drawing, wherein like numerals represent like parts throughout the several views, one embodiment of the dental device of the present invention is designated generally as 10. Device 10 includes a tongue retractor and shield member 12. Shield member 12 is formed of a flexible elastomeric material, which in the peferred embodiment is a foam material having spongelike or liquid absorbent characteristics as will be described in more detail hereafter. It will be understood that member 12 may be made of any suitable relatively flexible material, however. Shield member 12 has a central portion 14, an upper palatal portion 16, and a lower lingual portion 18. The edges of lingual portion 18 and palatal portion 16 curve inwardly with respect to a central horizontal axis drawn through shield member 12 from the front end toward the rear end of member 12. Extending rearwardly from central portion 14 is a throat guard member 20 which has a width measured generally in a direction transverse to the aforementioned axis of shield member 12 substantially smaller than the width of shield member 12 measured at central portion 14. Throat guard member 20 terminates in a fastening strip 22 having upper and lower ends 24 and 26, respectively. A flexible supporting stay, which is preferably a strip of plastic material, is affixed within fastening strip 22. It will be understood that in the preferred embodiment, shield member 12, throat guard member 20, and fastening strip 22 are integrally formed of the flexible elastomeric material.

A saliva collecting and removal means that includes a tube 30 is affixed to one side of shield member 12 in the embodiment illustrated in the drawings. Tube 30 is a plastic tube that may be affixed to shield member 12 by any suitable adhesive means and as shown in side elevation is C-shaped. Tube 30 has an upper end 32 which may be either closed or open and a lower end 34 which is connected to a vacuum suction device (not shown). Tube 30 has a top portion 36 affixed to palatal portion 16 and a bottom portion 38 affixed to lingual portion 18 and a central portion 39 disposed proximate the juncture of shield member 12 and guard member 20. Bottom portion 38 is provided with a plurality of apertures 40 spaced from approximately the middle central portion 39 of tube 30 along portion 38 to lower end 34. Top portion 36 has a forwardly extending portion 42 which extends beyond the front edge of shield member 12.

As shown in more detail in FIG. 5, a wire 46 is received within tube 30 and extends between upper end 32 and lower end 34. Wire 46 provides structural rigidity to the flexible elastomeric material of the shield member 12 in addition to securing shield member 12 in place within the mouth and aiding in holding the mouth open during the dental operation as will be described in more detail hereafter.

In the embodiment shown in FIG. 1, a tube 30 is affixed to one side of shield member 12. Alternatively, tube 30' may be imbedded within the flexible elastomeric material forming shield member 12' as illustrated in FIG. 1A. The flexible elastomeric material is selected to have sponge-like characteristics such that saliva will be absorbed by the material and extracted through tube 30'. In the embodiment wherein tube 30' is imbedded with the elastomeric material, apertures 41 may be provided on each side of shield member 12' in the flexible elastomeric material aligning generally with apertures 40 in tube 30' to facilitate the collection and removal of saliva. The embodiment shown in FIG. 1 wherein tube 30 is affixed to one side of shield member 12 is specifically designed for placement within one side of the mouth. For example, device 10 shown in FIGS. 1-7 is designed for placement in the right side of the patient's mouth. Tube 30 must be placed on the opposite side of shield member 12 than that shown in the drawings in order to form a device for placement in the left side of the patient's mouth. On the other hand, in the embodiment shown in FIG. 1A, device 10' could be utilized on either side of the patient's mouth.

The placement of dental device 10 within the mouth is illustrated in FIGS. 6 and 7. Device 10 is placed in a generally vertical orientation within the mouth with shield member 12 between the inner surfaces of teeth 48 and tongue 50. Palatal portion 16 is in contact with the roof of the mouth while lingual portion 18 engages the floor of the mouth. Device 10 is sized so that in placement of device 10 in the mouth ends 32 and 34 of tube 30 must be compressed toward each other, thereby applying a compressive force on wire 46. When device 10 is secure within the mouth, wire 46 has a tendency to regain its non-compressed state and therefore is resiliently biased against the roof and floor of the mouth. The biasing force is not sufficient to create significant patient discomfort, but assist in maintaining the patient's mouth open in addition to firmly securing shield member 12 in place. Since shield member 12 is formed of a flexible elastomeric material, the engagement of the palatal portion 16 and lingual portion 18 with the roof and the floor of the mouth, respectively, also creates a minimum of patient's discomfort. When using dental device 10, it is neither necessary nor desirable to provide a liquid-type seal at palatal portion 16 and lingual portion 18. Shield member 12 effectively protects tongue 50 from dental operations occurring on teeth 48. Wire 46 provides shield member 12 with sufficient structural.

Throat guard member 20 and fastening strip 22 are folded forward so that fastening strip 22 may be secured to an interior surface 52 of the patient's cheek with a suitable dental adhesive. Throat guard member 20 extends generally between the distal surface of the rear molars 56 and the ascending ramus (not shown) of the mandible or jawbone. With the patient's head tilted backward, throard guard member 20 effectively prevents debris generated by the dental operations from falling into the patient's throat. Of course, shield member 12 also aids in preventing debris from entering the throat. With the patient's head tilted backward, saliva has a tendency to pool generally in an area from the middle of tube 30 downward along the bottom portion 38 of tube 30. The pool of saliva is collected through apertures 40 of tube 30 and discharged through lower end 34.

FIGS. 8-12 illustrate an alternative embodiment of the present invention designated generally at 100. The embodiment illustrated in FIGS. 8-12 is a dental shield for isolating the region of the mouth and includes a shield member 102. Shield member 102 is generally planar and has connected thereto a palatal member 104 and a lingual member 106. Extending generally rearwardly of shield member 102 is an elongated throat protecting member 108. It is contemplated that shield 100 may also be constructed without throat protecting member 108. In the preferred embodiment, shield member 102, palatal member 104, lingual member 106 and throat protecting member 108 (when included), are molded of a suitable plastic material. Thus, in the preferred embodiment shield member 102, palatal member 104, lingual member 106 and throat protecting member 108 are integrally connected to each other. Palatal member 104 is a rod-like member that extends generally upward and outward from shield member 102. Spaced apart along the top of palatal member 104 are a plurality of projections, 110. The plastic material of which palatal member 104 is made is selected to have sufficient elastic and resilient characteristics such that palatal member 104 will bend generally about its point of connection 112 to shield member 102 to permit pivotal movement of palatal member 104 about point 112 toward and away from lingual member 106.

Lingual member 106 is preferably tubular having an open end at 114 and a plurality of apertures 116 formed in the wall thereof. In the embodiment shown in FIG. 8 apertures 116 are disposed generally at the lowermost and rearmost portions of dental shield 110. Spaced apart along the bottom of lingual member 106 are a plurality of projecting members 118. Lingual member 106 has a portion 107 extending downwardly and rearwardly with respect to a front portion 109 such that portion 107 and a lower portion 111 of shield member 102 is positioned below the occlusal plane of the patient's lower teeth and are engaged between the tongue and the inner aspect of the lower jaw when shield 100 is in place within the mouth. In operation, lingual member 106 is connected to a vacuum source at opening 114 and saliva that pools in the patient's mouth is collected through apertures 116 and ejected from the mouth through lingual member 106 and opening 114.

Dental shield 100 may be utilized with or without a cover member 120. Cover member 120 includes two pieces of preferably nonwoven fabric 122 and 124 that are sewn together and have an opening at 126. Cover member 120 is sized to fit over shield 100 as shown in dashed lines in FIG. 8. The fabric of which cover member 120 is made is selected to be relatively porous and flexible to permit the passage of saliva therethrough such that saliva can be collected through apertures 116 in lingual member 106.

FIGS. 11 and 12 illustrate placement of dental shield 100 in the patient's mouth in a substantially vertical orientation between the inside of the patient's teeth 128 and the patient's tongue 130. In FIGS. 11 and 12, cover 120 is shown in place, but it is to be understood that dental shield 100 may be utilized with or without cover 120. When used without cover 120 shield member 102 functions to retract the patient's tongue 130 and protect the tongue from the dental work area. Throat protecting member 108, when included as a part of shield 100, can be folded as shown in more detail in FIG. 12 and as described with respect to the previously described two alternative embodiments.

Projections 110 and 118 on palatal member 104 and lingual member 106, respectively, are spaced apart generally so that selective ones of the patient's upper and lower teeth will be received between the projections to more firmly secure shield 100 within the mouth and prevent shield 100 from slipping out of the proper position in the mouth. Shield 100 may be formed of a suitable plastic material to provide substantial flexibility of palatal member 104 permitting palatal member 104 to bend about point 112. When shield 100 is placed within the patient's mouth palatal member 104 is bent downward toward lingual member 106. In the relaxed state shown in FIG. 8 palatal member 104 is biased generally upward and away from lingual member 106 and will tend to return to the position shown in FIG. 8 when unstressed. When shield 100 is placed in the mouth bending palatal member 104 downward, palatal member 104 is placed under stress against the upward inherent biasing force of the plastic material. Dental shield 100 is thus held in compressive engagement within the mouth with palatal member 104 compressively engaging the roof of the mouth and lingual member 106 engaging the floor of the mouth. Palatal member 104 is provided with enough flexibility so that the patient may, if he so desires, or is so directed by the dentist, completely close his mouth with dental shield 100 still in place within the mouth. This features provides for significantly more patient comfort than previous prior art tongue retractor and/or saliva ejector devices.

From the above description, it can be seen that the present invention provides a dental device that effectively isolates the work area in the mouth for dental operations, shielding and retracting the patient's tongue, protecting the throat from debris created by the dental operations, and collecting and removing saliva from the mouth. Additionally, the device assists in keeping the patient's mouth open during the dental operations and causes a minimum of patient discomfort. In keeping with the modern trend toward sterile and disposable medical and dental devices, the present invention is formed of low-cost materials minimizing manufacturing expense and retail price. Thus, a dental practitioner can purchase relatively large quantities of the subject dental device at low cost so that the device can be simply used on a one time basis and discarded.

What is claimed is:

1. A dental device adapted to be placed in the mouth in substantially vertical orientation generally between the inside of the lower teeth and the tongue, comprising:
   (a) a frame to retain said device in the mouth, said frame further comprising:
       (i) a palatal member adapted to engage the mouth generally at the roof thereof;
       (ii) a lingual member connected to said palatal member to engage the mouth generally at the floor thereof; said lingual member having a first portion adapted to be disposed generally above the mandibular occlusal plane and to extend outward to engage the lower teeth and a second portion adapted to extend generally downward below the mandibular occlusal plane to engage the floor of the mouth;
   (b) a shield member affixed to said second portion and sized to shield the tongue from the lower teeth whereby the tongue pressing against said shield member serves to stabilize said device against lateral displacement in the mouth with said second portion retained against the inside of the gums below the teeth;
   (c) means for resiliently biasing said palatal and lingual members in a direction away from each other whereby upon placement of said device in the mouth said device is in compressive engagement between the floor and roof thereof; and
   (d) means on said palatal member and said first portion of said lingual member for engaging the patient's teeth.

2. A dental device in accordance with claim 1 wherein said engaging means comprises a plurality of projections spaced on said palatal and lingual members.

3. A dental device in accordance with claim 1 wherein said lingual member is a tubular member and said second portion thereof has a plurality of apertures therein, said first portion having an opening through which saliva collected in said tubular member through said apertures can be ejected from the mouth.

4. A dental device in accordance with claim 1 further comprising a throat protecting member connected to said frame and extending rearwardly from said frame and adapted to be folded forwardly to extend between the distal surfaces of the rear molars and the interior border of the ascending ramus of the mandible at one side of the mouth.

5. A dental device in accordance with claim 1 wherein said shield member is a substantially rigid planar member affixed to said palatal member at said second portion.

6. A dental device for isolating a region of the mouth and adapted to be placed in the mouth in substantially vertical orientation comprising:
   (a) a shield member adapted to be disposed between the patient's teeth and tongue;
   (b) a lingual member connected to said shield member generally at the bottom thereof, said lingual member having a plurality of projections spaced apart thereon to engage selected ones of the patient's lower teeth;
   (c) a palatal member connected to said shield member generally at the top thereof, said palatal member having a plurality of projections spaced apart thereon to engage selected ones of the patient's upper teeth, said lingual and palatal members connected to said shield member to permit movement generally toward and away from each other;

(d) means for resiliently biasing said palatal and lingual members in a direction away from each other whereby upon placement of said shield within the mouth said shield is placed in compressive engagement between the roof and floor of the mouth; and (e) a throat protecting member connected to and extending rearwardly from said shield member and adapted to be folded in a direction toward said shield member and to extend between the distal surfaces of the rear molars and the interior border of the ascending ramus of the mandible at one side of the mouth.

7. A dental shield in accordance with claim 6 wherein said lingual member comprises a tubular portion having an opening at one end thereof and a plurality of apertures therein whereby saliva can be collected through said apertures and ejected from the mouth through said opening.

8. A dental shield in accordance with claim 6 wherein said shield is formed of plastic material and wherein said palatal member comprises a rod pivoted generally about the connection of said palatal member to said shield member, the inherent elastic properties of said plastic material providing a biasing force urging said rod to an unstressed position in a direction away from said lingual member whereby upon placement of said shield member in the mouth said rod is secured in compressive engagement with the roof of the mouth.

9. A dental shield for isolating a region of the mouth and adapted to be placed in the mouth in substantially vertical orientation, comprising:

(a) a shield member adapted to be disposed between the patient's teeth and tongue;

(b) a lingual member connected to said shield member generally at the bottom thereof, said lingual member having a plurality of projections spaced apart thereon to engage selected ones of the patient's lower teeth;

(c) a palatal member connected to said shield member generally at the top thereof, said palatal member having a plurality of projections spaced apart thereon to engage selected ones of the patient's upper teeth, said lingual and palatal members connected to said shield member to permit movement generally toward and away from each other;

(d) means for resiliently biasing said palatal and lingual members in a direction away from each other whereby upon placement of said shield within the mouth said shield is placed in compressive engagement between the roof and floor of the mouth; and (e) a cover removably mounted to said shield member, said cover sized at least as large as said shield member and formed of relatively flexible material.

* * * * *